Figure 1:
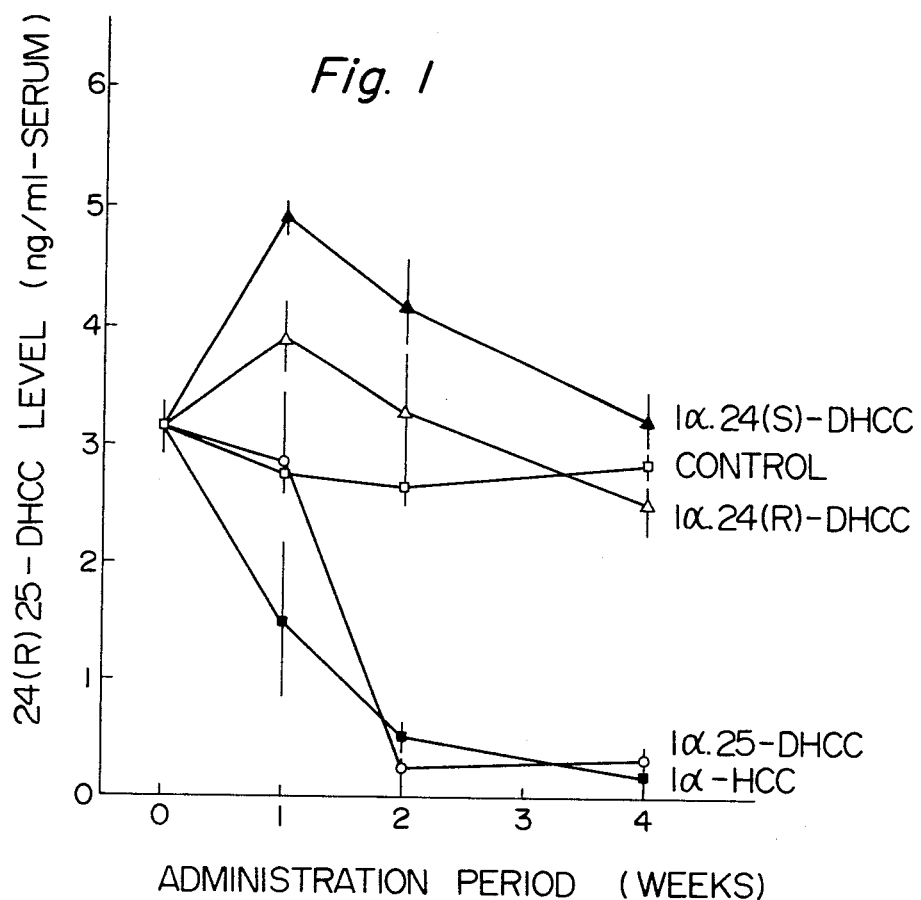

United States Patent [19]

Kiyoki et al.

[11] 4,364,941

[45] Dec. 21, 1982

[54] METHOD FOR REGULATING BONE METABOLISM OF WARM-BLOODED ANIMALS, AND PHARMACEUTICAL COMPOSITIONS THEREOF

[75] Inventors: Mamoru Kiyoki, Ohme; Hiroyoshi Endo, Kanagawa; Tatsuyuki Naruchi, Hino; Yoshinobu Hashimoto, Fujisawa, all of Japan

[73] Assignees: Teijin Limited, Osaka; Teijin Pharmaceutical Co., Ltd., Tokyo, both of Japan

[21] Appl. No.: 297,975

[22] Filed: Aug. 31, 1981

Related U.S. Application Data

[63] Continuation of Ser. No. 137,755, Apr. 7, 1980, abandoned.

[30] Foreign Application Priority Data

Apr. 10, 1979 [JP] Japan ................................ 54-42447

[51] Int. Cl.$^3$ ............................................. A61K 31/59
[52] U.S. Cl. ................................................... 424/236
[58] Field of Search ........................ 424/236; 260/397.2

[56] References Cited

U.S. PATENT DOCUMENTS

| | | | |
|---|---|---|---|
| 4,021,423 | 5/1977 | Baggiolini et al. | 424/236 |
| 4,022,891 | 5/1977 | Takeshita et al. | 260/397.2 |
| 4,305,935 | 12/1981 | Kawashima et al. | 424/236 |

OTHER PUBLICATIONS

Chem. Abstracts, vol. 91 (1979) Par. 598(e), Abstract of an article by Lieberheer et al.
Chem. Abstracts, vol. 90 (1979) Par. 70.874, Abstract of an article by Queille et al.

*Primary Examiner*—Elbert L. Roberts
*Attorney, Agent, or Firm*—Wenderoth, Lind & Ponack

[57] ABSTRACT

A method for regulating the bone metabolism of a warm-blooded animal, which comprises administering pharmaceutically effective amounts of 1α, 24-dihydroxycholecalciferol (1α, 24-DHCC) and 24,25-dihydroxycholecalciferol (24,25-DHCC) to said warm-blooded animal, and a pharmaceutical composition comprising 1α,24-DHCC, 24,25-DHCC and a pharmaceutically acceptable carrier.

According to the invention, a condition of abnormal bone metabolism requiring long-term therapy, such as osteoporosis, can be safely treated by administering 1α, 24-DHCC and 24,25-DHCC over a long period of time because no substantial adverse effect of 1α, 24-DHCC on the metabolis of 24,25-DHCC is observed.

13 Claims, 4 Drawing Figures

METHOD FOR REGULATING BONE METABOLISM OF WARM-BLOODED ANIMALS, AND PHARMACEUTICAL COMPOSITIONS THEREOF

This application is a continuation of application Ser. No. 137,755, filed Apr. 7, 1980 now abandoned.

This invention relates to a method for regulating the bone metabolism of warm-blooded animals. More specifically, this invention relates to a method for regulating the bone metabolism of warm-blooded animals by administering 1α,24-dihydroxycholecalciferol and 24,25-dihydroxycholecalciferol to said warm-blooded animals, and to a pharmaceutical composition comprising 1α,24-dihydroxycholecalciferol and 24,25-dihydroxycholecalciferol for regulating the bone metabolism of warm-blooded animals and a pharmaceutically acceptable carrier.

The concentration of calcium in the serum of a warm-blooded animal having a normal function of calcium metabolism is maintained at a constant level by the subtle regulation of calcium absorption in the intestinal tract, bone resorption and bone formation in the bone tissues and renal calcium excretion. When the concentration of calcium in the serum deviates from a normal fixed level, calcium absorption from the intestinal tract and bone resorption and bone formation in the bone tissues, and excretion of calcium from the kidneys are spontaneously regulated in order to return to the normal fixed level.

It is well known that 1α,25-dihydroxycholecalciferol, parathyroid hormone (PTH), and calcitonin (CT) as a hormone secreted from the thyroid gland are among in vivo substances involved in the regulation of such actions (Federation Proceedings 37, No. 12, October 1978, pages 2557–2560). It is also known that 1α,24-dihydroxycholecalciferol, a synthetic product, promotes calcium absorption from the intestinal tract and bone resorption from the bone tissues (U.S. Pat. No. 4,022,891).

A fixed calcium concentration in the serum has a crucial role in maintaining the living organism physiologically normal because any deviation of the serum calcium level from the fixed value is undesirable in maintaining the living body.

When calcium absorption in the intestinal tract cannot provide a sufficient amount of calcium to maintain the concentration of calcium in the serum at a normal level, the living body dissolves its own bones. Such a function of the living body means that even when the serum calcium concentration is maintained at a normal fixed level, the bone tissues are not always normal. It teaches that although the proper functioning of the bone tissues is not irrelevant to the concentration of the calcium in the serum, it cannot be achieved only by the proper adjustment of the calcium level in the serum.

The bone tissues in a living body are maintained normal when the bone resorption and bone formation proceed always concurrently, and are equilibrated with normal metabolism. In the event that the equilibrium between bone resorption and bone formation is lost by some abnormality in calcium metabolism in vivo, a disorder of the bone tissues, such as the increase or decrease of the amount of bone mass, would occur.

It is known that the concentration of calcium in the serum, the concentration of phosphoric acid in the serum, biologically active vitamin $D_3$ anologs, PTH, CT, etc. are in vivo factors which affect bone metabolism, i.e. bone resorption and bone formation. In actual bone metabolism in vivo, these factors are considered to work together complicatedly. The state of these factors has been elucidated to some extent, but its entire aspect has not yet been known.

There has been a significant increase in the population of the old in recent years, and many old persons including those with renal failure suffer from derangement of bone metabolism. It has been the social need to make investigations for remedying derangement of bone metabolism.

Kanis et al. reported that when 24,25-dihydroxycholecalciferol administered to patients with various disorders of mineral metabolism calcium balance increased and suggested that 24,25-dihydroxycholecalciferol may be an important regulator of skeletal metabolism; [British Medical Journal, 1, 1382–1386 (1978)].

Goodwin et al. reported that when 1α-hydroxycholecalciferol and 24,25-dihydroxycholecalciferol were administered to chicks with ricket, the number of osteoclasts in the metaphysis of bones decreased as compared with the case of administering 24,25-dihydroxycholecalciferol alone, and exhibits almost the same number of osteoclasts as in the case of administering vitamin $D_3$, and that the pattern of the bone tissues (in a photograph) was better than in the case of administering only 24,25-dihdroxycholecalciferol; and concluded that 24,25-dihydroxycholecalciferol is an essential ingredient for bone formation [see Nature, 276, 30th November (1978), pp. 517–519].

According to these literature references, 24,25-dihydroxycholecalciferol seems to be an essential ingredient for bone formation. But these references teach that bone formation can substantially take place to an observable degree only when it is administered in combination with 1α,25-dihydroxycholecalciferol or 1α-hydroxycholecalciferol.

Investigations of the present inventors have shown that the concentration of 24,25-dihydroxycholecalciferol in the serum decreases upon a long-term administration of 1α-hydroxycholecalciferol and/or 1α,25-dihydroxycholecalciferol to a living organism. Accordingly, when administered together with 24,25-dihydroxychlocalciferol, 1α-hydroxycholecalciferol or 1α,25-dihydroxycholecalciferol makes some contribution to the conversion of the administered 24,25-dihydroxycholecalciferol considered to be essential for bone formation into another metabolite, and therefore it is thought that 1α-hydroxycholecalciferol or 1α,25-dihydroxycholecalciferol is not entirely desirable for sufficient exhibition of the bone forming action of 24,25-dihydroxycholecalciferol when administered in combination therewith.

It is an object of this invention therefore to provide a method for regulating the bone metabolism of warm-blooded animals.

Another object of this invention is to provide a method for remedying or preventing derangement of bone metabolism of warm-blooded animals.

Still another object of this invention is to provide a novel combination of active vitamin $D_3$ anologs which can be safely administered to warm-blooded animals over a long period of time to regulate their bone metabolism.

A further object of this invention is to provide a novel combination of active vitamin $D_3$ anologs for regulating the bone metabolism of warm-blooded animals which permits a high ratio of utilization of active vitamin D₃ analogs in vivo.

Other objects and advantages of this invention will become apparent from the following description.

According to the broadest concept of this invention, the objects and advantages of this invention are achieved by a method for regulating the bone metabolism of warm-blooded animals, which comprises administering pharmaceutically effective amounts of 1α,24-dihydroxycholecalciferol and 24,25-dihydroxycholecalciferol to the warm-blooded animals.

1α,24-dihydroxycholecalciferol (to be abbreviated 1α,24-DHCC) and 24,25-dihydroxycholecalciferol (to be abbreviated 24,25-DHCC) are known as active vitamin D₃, but to the best of the knowledge of the present inventors, there has been no literature reference which clearly states that administration of a combination of these vitamin D₃ anologs advantageously causes bone formation.

The 1α,24-DHCC used in this invention is 1α,24(R)-DHCC of the following formula (1) in which the hydroxyl group at the 24-position has an R-configuration

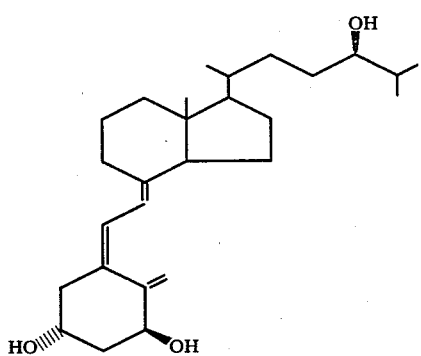

or 1α,24(S)-DHCC of the formula (2) in which the hydroxyl group at the 24-position has an S-configuration

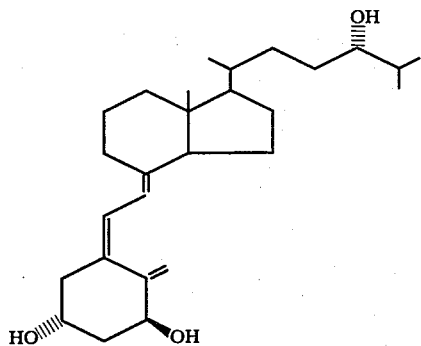

or a mixture in arbitrary proportions of 1α,24(R)-DHCC and 1α,24(S)-DHCC.

Likewise, 24,25-DHCC used in this invention is 24(R),25-DHCC of the following formula (3)

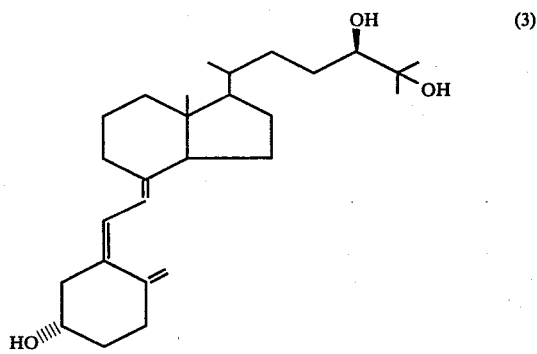

or 24(S),25-DHCC expressed by the following formula (4).

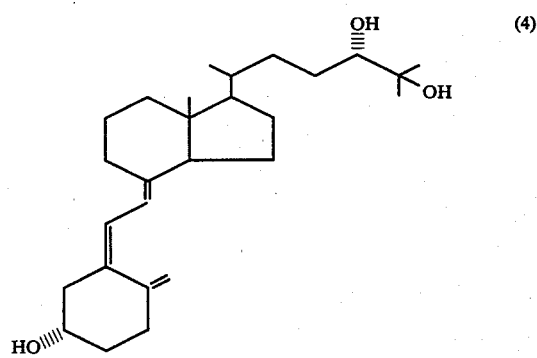

or a mixture in arbitrary proportions of 24(R),25-DHCC and 24(S),25-DHCC.

Investigations of the present inventors have substantially shown that when these active vitamin D₃ anologs are used in an in vitro bone tissue culture, they exhibit the following sequence of activity.

1α,24(R)-DHCC+24(R),25-DHCC>
1α,24(R)-DHCC+24(RS),25-DHCC>
1α,24(RS)-DHCC+24(R),25-DHCC>
1α,24(RS)-DHCC+24(RS),25-DHCC>
1α24(R)-DHCC+24(S),25-DHCC≧
1α,24(RS)-DHCC+24(S),25-DHCC≧
1α,24(S)-DHCC+24(R, S or RS)-DHCC

In the above formulae, the symbol (RS) represents a racemic mixture of R-form and S-form.

The above tendency shows that the activities of 1α,24-DHCC and 24,25-DHCC used in this invention increase as the concentration of the R-form increases.

The active vitamin D₃ anologs used in this invention can be produced, for example, by the methods described in U.S. Pat. No. 4,022,891 and Tetrahedron Letters 1, pages 15–18 (1975). These documents are cited herein as references.

In the present application, the term "bone metabolism" denote bone resorption and bone formation. Accordingly, "to regulate bone metabolism" in this Application is, for example, to inhibit bone resorption when it is accelerated, or to accelerate bone resorption when it is inhibited, or to accelerate bone resorption and bone formation when both are inhibited. In other words, it is to bring abnormal bone metabolism to a normal one, or to maintain normal bone metabolism.

The present invention is preferably applicable when bone formation is inhibited either alone or together with bone resorption. The present invention can also be applied for prophylactic purposes when a condition possibly affecting bone resorption or bone formation is likely to derange bone metabolism in future.

The derangement of bone metabolism to which the present invention is applicable is, for example, a condition involving a decrease in the weight of bones, or a condition which impairs the normal reactivity of bones with calcium homeostatic hormones. Specific examples of these conditions are vitamin D-dependent rickets, renal osteodystrophy, hypoparathyroidism, osteoporosis, osteomalacia, Peget's disease, malabsorption syndrome, hypocalcemia induced by liver cirrhosis, hypocalcemia induced by stearorrhoea, hypocalcemia caused by vitamine D-resistant rickets, abnormal metabolism of calcium and phosphorus caused by liver failure, renal failure, gastrointestinal tract failure or parathyroid failure, and related bone diseases.

The conditions leading to abnormal bone metabolism, to which the present invention is applicable for prophylactic purposes, are, for example, ovarectomy, nephrectomy, or a condition in which steroid hormones such as hydrocortisone are being administered.

The present invention can be applied preferably to man. It can also be applied to other warm-blooded animals, for example cows during or immediately before delivery and swines for prevention of bone diseases that may be induced by hypocalcemia.

In the present invention, $1\alpha,24$-DHCC and $24,25$-DHCC can be administered together to a warm-blooded animal. Alternately, $1\alpha,24$-DHCC may be first administered, and after a suitable period of time, $24,25$-DHCC may be administered. Preferably, they are administered together.

The active vitamin $D_3$ analogs are administered in parmaceutically effective amounts, for example 1 to 1000 ng/day/kg, preferably 2 to 100 ng/day/kg, for $1\alpha,24$-DHCC, and 10 to 2,000 ng/day/kg, preferably 20 to 1,000 ng/day/kg for $24,25$-DHCC.

In the present invention, these active vitamin $D_3$ anologs can be administered once, or several times, for example two or three times, a day. The number of administrations may be determined depending upon the condition of a particular warm-blooded animal to be treated. In the case of man, it may be determined by physicians, and in other warm-blooded animals, it may be determined by veterinarians or by producers, owners, etc. under the guidance and supervision of veterinarians.

Investigations of the present inventors have shown that as already stated hereinabove and to be described in examples given hereinbelow, a condition of abnormal bone metabolism requiring long-term therapy, such as osteoporosis, can be safely treated by administering $1\alpha,24$-DHCC and $24,25$-DHCC over a long period of time because no substantial adverse effect of $1\alpha,24$-DHCC on the metabolism of $24,25$-DHCC is observed. This is an advantage of the present invention over a method involving the use of $1\alpha$,hydroxycholecalciferol or $1\alpha,25$-dihydroxycholecalciferol in combination with $24,25$-DHCC. This advantage of the invention is achieved especially preferably by administering $1\alpha,24$-DHCC and $24,25$-DHCC while maintaining the concentration of calcium in the serum of warm-blooded animals at 8 to 12 mg/dl of serum, preferably 8.5 to 11 mg/dl of serum.

By administering pharmaceutically effective amounts of $1\alpha,24$-DHCC and $24,25$-DHCC to an animal, they exert an excellent effect on bone metabolism, especially on bone formation. These vitamin $D_3$ anologs can be administered through various routes. Specifically, $1\alpha,24$-DHCC and $24,25$-DHCC may be administered orally or parenterally (e.g. intramuscularly, intravenously, subcutaneously or intrarectally, preferably orally.

The $1\alpha,24$-DHCC and $24,25$-DHCC are administered either singly or as a mixture to warm-blooded animals, especially man, requiring normal bone metabolism.

Desirably, these active vitamin $D_3$ anologs are administered as a mixture with a pharmaceutically acceptable carrier.

According to this invention it is desirable to administer $1\alpha,24$-DHCC and $24,25$-DHCC together, and thus, there is provided a pharmaceutical composition comprising $1\alpha,24$-DHCC and $24,25$-DHCC and a pharmaceutically acceptable carrier. Such a pharmaceutical composition comprising both $1\alpha,24$-DHCC and $24,25$-DHCC which act favorably on bone metabolism of warm-blooded animals has not been known in the past. It has been provided for the first time by the present inventors on the basis of the fact that $1\alpha,24$-DHCC and $24,25$-DHCC show a very good cooperative action, as discovered by the present inventors.

Examples of the pharmaceutically acceptable carrier are those which give liquid pharmaceutical compositions, for example ethyl alcohol, vegetable oils (e.g., corn oil, olive oil, cotton seed oil, coconut oil, almond oil and peanut oil), fish liver oil and oily esters (e.g., polysorbate 80); those which give solid pharmaceutical compositions melting at the body temperature of warm-blooded animals, for example cacao butter, or other fatty acid triglycerides; those which give solid pharmaceutical compositions not meltable at the body temperature of warm-blooded animals, such as calcium carbonate, potato starch, alginic acid or lactose; and those which give aqueous or non-aqueous solutions or suspensions, for example propylene glycol, polyethylene glycol, and organic acid esters such as ethyl oleate.

The pharmaceutical compositions of this invention contain the active vitamin $D_3$ anologs in small proportions. Thus, for ease of formulation, they are preferably used in combination with carriers that give solutions or dispersions.

The pharmaceutical composition of this invention may contain anti-oxidants such as ascorbic acid, butylated hydroxy anisole or hydroquinone to stabilize the active-forms of vitamin $D_3$ which are unstable to oxidation or light. Or the active vitamin $D_3$ analogs may be incorporated as inclusion compounds of cyclodextrins such as $\beta$-cyclodextrin.

According to this invention, there is also provided a medicament in unit dosage form composed of a pharmaceutical composition comprising $1\alpha,24$-DHCC and $24,25$-DHCC.

Such a medicament is in the form of, for example, tablets, pills, sugar-coated tablets, hard or soft gelatin capsules, buccal tablets, suppositories, and injections. Hard or soft gelatin capsules are preferred.

The medicament is usually provided as a medicament comprising 0.05 to 2.5 g of $1\alpha,24$-DHCC and 0.5 to 25 g of $24,25$-DHCC, preferably a medicament in the form of soft or hard gelatin capsules for oral administration.

In the present invention, $1\alpha,24$-DHCC and $24,25$-DHCC may have both R and S configurations at the 24-position. Preferably, at least one of $1\alpha,24$-DHCC and $24,25$-DHCC has an R configuration at the 24-position. Especially preferably, at least $1\alpha,24$-DHCC has an R configuration at the 24-position. Above all, a combination of 1α,24(R)-DHCC and 24(R),25-DHCC is preferred.

The following examples illustrate the present invention more specifically. It should be noted however that these examples are not intended in any way to limit the present invention.

EXAMPLE 1

(1) Each of the following active vitamin $D_3$ anologs,
1α-hydroxycholecalciferol (abbreviated 1α-HCC),
1α,25-dihydroxycholecalciferol (abbreviated 1α,25-DHCC),
1α,24(R)-DHCC, and
1α,24(S)-DHCC,
was administered orally once a day as a solution dissolved in an aqueous solution containing a small amount of ethanol and 0.1% of Triton X-100 to 12-week old normal Wistar rats (male) in groups each consisting of three rats. The dosage was 0.1 μg/kg/day. Only the aqueous solution was administered to a control group. The period of administration was 1, 2 and 4 weeks, respectively. Twenty-four hours after the final administration, blood was taken out from the descending aorta, and serum was obtained from the blood in a customary manner.

The content of 24(R), 25-DHCC in the serum samples was determined by a competitive protein binding assay method using the kidney cytosol of vitamin D-deficient rats [see Biochem. Biophys. Res. Comm., 70, No. 4 (1976) pp 1243–1249]. The content of calcium in these serum samples was determined by the OCPC method [see. Am. J. Clin. Pathol, Vol. 45, pages 290–296 (1966)].

The results are shown in Table 1 and FIG. 1. FIG. 1 shows the level of 24(R),25-DHCC alone.

TABLE 1

| Active vitamin $D_3$ administered | Administration period (weeks) | Content of 24(R),25-DHCC in the serum (ng/ml ± S.E.) | Calcium content in the serum (ng/ml ± S.E.) |
|---|---|---|---|
| Control | 0 | 3.14 ± 0.19 | 10.3 ± 0.2 |
|  | 1 | 2.77 ± 0.15 | 10.2 ± 0.2 |
|  | 2 | 2.64 ± 0.12 | 10.3 ± 0.2 |
|  | 4 | 2.84 ± 0.07 | 10.2 ± 0.1 |
| 1α-HCC | 1 | 1.48 ± 0.09 | 11.6 ± 0.2 |
|  | 2 | 0.51 ± 0.10 | 11.6 ± 0.0 |
|  | 4 | 0.17 ± 0.05 | 11.2 ± 0.1 |
| 1α,25-DHCC | 1 | 2.84 ± 0.59 | 11.2 ± 0.1 |
|  | 2 | 0.22 ± 0.05 | 11.7 ± 0.1 |
|  | 4 | 0.31 ± 0.10 | 11.1 ± 0.2 |
| 1α,24(R)-DHCC | 1 | 3.89 ± 0.29 | 11.3 ± 0.2 |
|  | 2 | 3.28 ± 0.57 | 11.3 ± 0.2 |
|  | 4 | 2.51 ± 0.26 | 11.2 ± 0.3 |
| 1α,24(S)-DHCC | 1 | 4.93 ± 0.12 | 11.3 ± 0.1 |
|  | 2 | 4.18 ± 0.42 | 11.1 ± 0.5 |
|  | 4 | 3.19 ± 0.26 | 10.4 ± 0.2 |

(n = 3)

The following conclusions are drawn from the above results.

When the active vitamin $D_3$ anologs are administered, the level of calcium in the serum is slightly higher than the level of the control after a lapse of 1 week.

The level of 24(R),25-DHCC in the serum exhibits a different behavior according to the type of the active vitamin $D_3$ administered. When 1α-HCC and 1α,25-DHCC are administered, the level of 24(R),25-DHCC tends to decrease gradually to an undetectable level as the administration period increases. On the other hand, when 1α,24(R)-DHCC and 1α,24(S)-DHCC are administered, the 24(R),25-DHCC level in the serum is slightly higher than the level of the control, or shows an equivalent tendency.

It is anticipated from this that 1α,24(R)-DHCC or 1α,24(S)-DHCC makes a different contribution from 1α-HCC or 1α,25-DHCC to the formation or metabolism in vivo of 24(R),25-DHCC at almost the same calcium level.

(2) The present inventors further conducted the following experiment in order to clarify such an in vivo condition.

Each of 1α-HCC, 1α,25-DHCC, 1α,24(R)-DHCC and 1α,24(S)-DHCC was administered orally once a day to 11 week-old normal Nistar rats (male) in groups each consisting of three rats in the same way as in (1) above. The dosage was 0.1 μg/kg/day, and the administration was continued for 2 weeks. Twenty-four hours after the final administration, a solution of (26- and/or 27-$^3$H)25-hydroxycholecalciferol (11.7 Ci/mmole) in 50% ethanol-physiological saline was intravenously injected to the rats in a dosage of 17.6 ng/head (0.5 μCi/head). Twenty-four hours after the injection, blood was taken out, and serum was obtained.

Each of the serum samples was extracted with chloroform-methanol (1:1), and the lipid extract was fractionated by column chromatography on Sephadex LH-20 [developing solvent: chloroform-n-hexane (65:35) mixture]. The radio-activity of each fraction was measured, and the amount of [26-and/or 27-$^3$H]24(R),25-DHCC was determined.

The results are shown in Table 2.

TABLE 2

| Vitamin $D_3$ anolog administered | Content of [26- and/or 27-$^3$H] 24(R), 25-DHCC (f moles/ml ± S.E.) |
|---|---|
| Control | 94.3 ± 5.4 |
| 1α-HCC | 94.2 ± 6.6 |
| 1α,25-DHCC | 92.5 ± 4.9 |
| 1α,24(R)-DHCC | 118.3 ± 6.5 |
| 1α,24(S)-DHCC | 59.8 ± 4.6 |

(n = 3)

It is seen from the results that when 1α-HCC, 1α,25-DHCC and 1α,24(R)-DHCC are administered, 24,25-DHCC formed from the administered 25-HCC was contained in the serum at almost the same level as the control.

On the other hand, when 1α,24(S)-DHCC was administered, the serum contained [$^3$H]24,25-DHCC formed from the administered [$^3$H]25-DHCC at a lower level than the control.

The following discussions may be made on the basis of the results of Tables 1 and 2 taken together.

(1) 1α-HCC and 1α,25-DHCC appear to scarcely affect the process of production of 24(R),25-DHCC from 25-HCC in vivo, but are considered to promote the metabolism of the resulting 24(R),25-DHCC.

(2) 1α,24(R)-DHCC is considered to scarcely affect both the production of 24(R),25-DHCC from 25-HCC and the metabolism of the resulting 24(R),25-DHCC in vivo.

(3) 1α,24(S)-DHCC probably exerts slightly more effects on the formation of 24(R),25-DHCC from 25-HCC in vivo than does 1α-HCC, 1α,25-DHCC or 1α,24(R)-DHCC, but it is not deemed that it affects the metabolism of the produced 24(R),25-DHCC as greatly as 1α-HCC or 1α,25-DHCC.

It is clear from the above that foregoing that 1α,24(R)-DHCC and 1α,24(S)-DHCC, especially 1α,24(R)-DHCC, when administered to a living body together with 24,25-DHCC has a far greater activity of effectively retaining the administered 24,25-DHCC and 24,25-DHCC formed in vivo from 25-HCC within the living body than 1α-HCC or 1α,25-DHCC.

the femur was noted, but on the other hand, when 1α,24-DHCC and 24,25-DHCC were used in combination (Examples 2 to 4), the amount of calcium in the femur increased greatly, thus showing acceleration of calcium deposition.

TABLE 3

Calcium level of 9 day-old chick embryonic femur after 6 days' cultivation using PTH added basal medium as control

| | Treatment | Concentration (ng/ml) | Number | Calcium level (μg/femur) Control bones | Treated bones | Bone formation ratio* |
|---|---|---|---|---|---|---|
| Example 2 | 1α,24(R)-DHCC 24(R),25-DHCC | 0.02 0.5 | 10 8   10 | 4.84 ± 0.97 | 9.53 ± 0.78 | 1.93 ± 0.17** |
| Example 3 | 1α,24(RS)-DHCC 24(R),25-DHCC | 0.02 0.5 | 8 6   8 | 0.63 ± 0.25 | 9.22 ± 0.23 | 1.51 ± 0.22** |
| Example 4 | 1α,24(RS)-DHCC 24(RS),25-DHCC | 0.02 0.5 | 6 6   8 | 5.56 ± 0.90 | 6.90 ± 0.22 | 1.35 ± 0.20 |
| Comparative Example 1 | 1α,24(R)-DHCC | 0.02 | 6 | 6.67 ± 1.20 | 6.73 ± 0.98 | 1.03 ± 0.16 |
| Comparative Example 2 | 24(R),25-DHCC | 0.5 | 5 | 10.40 ± 0.39 | 9.52 ± 0.76 | 0.91 ± 0.10 |

The value represents a mean ± standard error.
Control femur was cultivated in the control medium.
*The ratio of treated femora to pair-mate control bones in calcium level
**Statistical significance $P < 0.01$ The results shown in Table 1 and FIG. 1 suggest that in long-term administration to man, a combination of 1α,24-DHCC and 24,25-DHCC can be administered without almost changing its dosage, but a combination of 1α-HCC (or 1α,25-DHCC) and 24,25-DHCC must be administered such that the dosage of 24,25-DHCC is gradually increased as the administration period is prolonged.

EXAMPLES 2 TO 4 AND COMPARATIVE EXAMPLES 1 AND 2

An embryo was taken out from 9 day-old eggs of white leghorn, and the left and right femora were enucleated under a dissecting microscope. The femora were attached to a glass roller-tube, and 1.5 ml of the following medium. The tube was placed in a rotary cultivator, and incubated at 37° C. for 6 days. The culture medium was exchanged every 48 hours.

Control medium: A mixture of 1 part by volume of an 11-day chick embryo extract (11-day CEE) and 9 parts by volume of a synthetic culture broth (BGJbHW2*) containing 1 U/ml of PTH. [*See "Connective Tissues", Vol. 6, page 139 (1974).]

Experimental medium: Obtained by adding active vitamin $D_3$ in the amounts indicated in Table 3 to the above control medium.

After cultivation, the bones were taken out, and washed several times with phosphate buffer saline [calcium ion free; PBS(−)]. Then, 0.1 ml of 2 N-HCl was added to dissolve calcium. The amount of calcium was determined by the OPCP method using a calcium assay kit (a product of Iatron Laboratories, Inc.). The results are shown in Table 3.

To allow differences between embryos Table 3 also shows the results obtained when one of the femora obtained from the same individual was used as a control.

Figure 2:
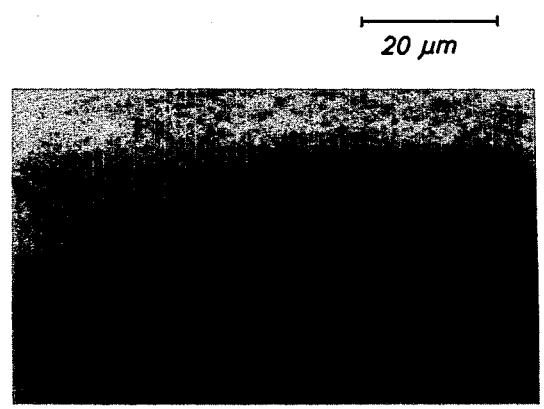
Figure 3:
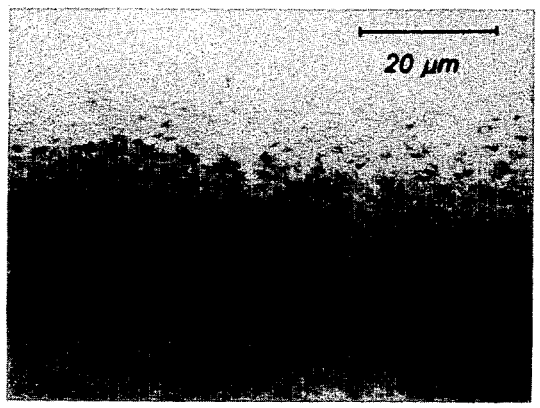
Figure 4:

It is seen from Table 3 that when 1α,24-DHCC or 24,25-DHCC was used singly (Comparative Examples 1 and 2), only some change in the amount of calcium in FIGS. 2, 3 and 4 show photographed patterns of the cultivated bone tissues obtained in Example 2 and Comparative Examples 1 and 2, respectively.

These photographs were obtained as follows: the bones were taken out from the cultivation tube, washed with PBS(−), and fixed with a 10% formalin solution, and embedded in paraffin. Thin test pieces having a thickness of about 10 microns were prepared, subjected to von Kossas stain, and photographed.

Taking of calcium into the bones can be observed from the tissue patterns.

A comparison of FIG. 2 with FIGS. 3 and 4 clearly shows that when 1α,24-DHCC and 24,25-DHCC were used together in accordance with this invention (FIG. 2), calcium was taken into the organic substrate of the bones forming a network structure (the intricate band-like portions seen black at the lower portion of the photograph of FIG. 2), and the periosteum (the entire photographed portion in FIG. 2) showed almost the same tissue pattern as physiological bone formation, as contrasted with the case of using these vitamin $D_3$ analogs singly (FIGS. 3 and 4).

What we claim is:

1. A method for regulating the bone metabolism of a warm-blooded animal, which comprises administering pharmaceutically effective amounts of 1α,24-dihydroxycholecalciferol and 24,25-dihydroxycholecalciferol to the warm-blooded animal, said amount being sufficient to bring abnormal bone metabolism to a normal bone metabolism or to maintain normal bone metabolism.

2. The method of claim 1 wherein said warm-blooded animal is man.

3. The method of claim 1 wherein said warm-blooded animal is other than man.

4. A method for remedying abnormal bone metabolism of a warm-blooded animal, which comprises administering pharmaceutically effective amounts of 1α,24-dihydroxycholecalciferol and 24,25-dihydroxycholecalciferol to the warm-blooded animal said amount being sufficient to bring abnormal bone metabolism to a normal bone metabolism.

5. The method of claim 4 wherein the abnormal bone metabolism involves a decrease in the amount of bonemass.

6. The method of claim 4 wherein the abnormal bone metabolism is the derangement of normal reactivity of bones with calcium homeostatic hormone.

7. A method for preventing the abnormal bone metabolism of a warm-blooded animal, which comprises administering pharmaceutically effective amounts of a 1α,24-dihydroxycholecalciferol and 24,25-dihydroxycholecalciferol to the warm-blooded animal said amount being sufficient to maintain normal bone metabolism.

8. A method for regulating the bone metabolism of a warm-blooded animal, which comprises administering pharmaceutically effective amounts of 1α,24-dihydroxycholecalciferol and 24,25-dihydroxycholecalciferol to said warm-blooded animal said amount being sufficient to bring abnormal bone metabolism to a normal bone metabolism or to maintain normal bone metabolism so that the calcium level in the serum of said warm-blooded animal is maintained at 8 to 12 mg/dl of serum.

9. A pharmaceutical composition for regulating the bone metabolism of a warm-blooded animal which comprises a pharmaceutically effective amount of a mixture of 1α,24-dihydroxycholecalciferol and 24,25-dihydroxycholecalciferol and a pharmaceutically acceptable carrier.

10. A medicament for regulating the bone metabolism of a warm-blooded animal in unit dosage form comprising a unit dosage of 1α,24-dihydroxycholecalciferol and 24,25-dihydroxycholecalciferol and a pharmaceutically acceptable carrier.

11. A medicament for oral administration for regulating the bone metabolism of a warm-blooded animal in unit dosage form comprising 0.05 to 10 μg of 1α,24-dihydroxycholecalciferol and 0.5 to 25 μg of 24,25-dihydroxycholecalciferol and a pharmaceutically acceptable carrier.

12. The medicament of claim 10 or 11 wherein the 1α,24-dihydroxycholecalciferol is 1α,24(R)-dihydroxycholecalciferol, 1α,24(S)-dihydroxycholecalciferol, or 1α,24(R,S)-dihydroxycholecalciferol.

13. The medicament of claim 10 or 11 wherein said 24,25-dihydroxycholecalciferol is 24(R),25-dihydroxycholecalciferol, 24(S),25-dihydroxycholecalciferol, or 24(R,S),25-dihydroxycholecalciferol.

* * * * *